(12) United States Patent
Weir et al.

(10) Patent No.: US 6,515,138 B2
(45) Date of Patent: Feb. 4, 2003

(54) TRANSESTERIFICATION PROCESS

(75) Inventors: William David Weir, Levittown, PA (US); Donald Robert Weyler, Levittown, PA (US); William Joseph Grieco, Collegeville, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 10/091,770

(22) Filed: Mar. 6, 2002

(65) Prior Publication Data

US 2002/0177719 A1 Nov. 28, 2002

Related U.S. Application Data

(60) Provisional application No. 60/276,589, filed on Mar. 16, 2001, and provisional application No. 60/284,020, filed on Apr. 16, 2001.

(51) Int. Cl.$^7$ .............................................. C07D 233/32
(52) U.S. Cl. .................................................... 548/324.1
(58) Field of Search ....................................... 548/324.1

(56) References Cited

U.S. PATENT DOCUMENTS

| | | | |
|---|---|---|---|
| 5,072,027 A | | 12/1991 | Kobayashi et al. |
| 5,883,261 A | * | 3/1999 | Esch et al. ............... 548/324.1 |
| 6,008,371 A | * | 12/1999 | Knebel et al. ........... 548/324.1 |
| 6,166,220 A | * | 12/2000 | Singh et al. ............. 548/313.4 |
| 6,179,906 B1 | * | 1/2001 | Marsella et al. ....... 106/287.21 |

FOREIGN PATENT DOCUMENTS

| | | |
|---|---|---|
| EP | 0 453 638 A1 | 10/1991 |
| EP | 0 650 962 A1 | 5/1995 |
| EP | 0 902 017 A1 | 3/1999 |

* cited by examiner

*Primary Examiner*—Deborah C. Lambkin
(74) *Attorney, Agent, or Firm*—Alan Holler

(57) ABSTRACT

An improved transesterification process is disclosed for forming certain (meth)acrylates by the transesterification of an alkyl (meth)acrylate with a hydroxyl alkyl imidazolidin-2-one using a transesterification catalyst in the presence of a polymerization inhibitor.

13 Claims, No Drawings

TRANSESTERIFICATION PROCESS

CROSS REFERENCE TO RELATED PATENT APPLICATIONS

This is a non-provisional application of prior pending U.S. provisional applications serial Nos. 60/276,589 filed Mar. 16, 2001 and 60/284,020 filed Apr. 16, 2001.

This invention relates to a process to prepare monomers, more specifically this invention relates to a transesterification process to prepare (meth)acrylate monomers.

It is known, for example in EP-A-0,902,017, that (meth) acrylates of Formula I, such as N-(2- methacryloyloxyethyl) ethylene urea (MEEU), and the alcohol of Formula IV, such as methanol, may be produced by the transesterification of an alkyl (meth)acrylate of Formula II, such as methyl methacrylate (MA) with a hydroxyl alkyl imidazolidin-2-one of Formula III, such as hydroxyethyl ethylene urea (HEEU), using a transesterification catalyst and in the presence of a polymerization inhibitor.

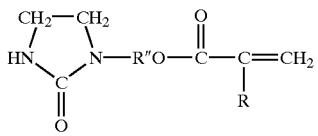

FORMULA I where R=H or $CH_3$;
where $R''=C_1-C_8$ straight or branched alkylene;

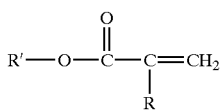

FORMULA II where R=H or $CH_3$; and
where $R'=C_1-C_8$ straight or branched alkyl;

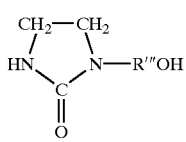

FORMULA III where $R''=C_1-C_8$ straight or branched alkylene;

 FORMULA IV where $R'=C_1-C_8$ straight or branched alkyl.

Conventionally, the transesterification catalyst is added to the well-mixed reaction mixture containing the alkyl (meth)acrylate of Formula II and the hydroxyl alkyl imidazolidin-2-one of Formula III. We have unexpectedly discovered that level of conversion of the hydroxyl alkyl imidazolidin-2-one of Formula III to the (meth) acrylate of Formula I may be increased for the above-described transesterification process by ensuring that the transesterification catalyst has ample opportunity to be in contact with the hydroxyl alkyl imidazolidin-2-one of Formula III by introducing the transesterification catalyst to the hydroxyl alkyl imidazolidin-2-one of Formula III while the reaction mixture is unagitated.

Statement of the Invention

We have discovered an improved process for forming the (meth)acrylate monomer of Formula I:

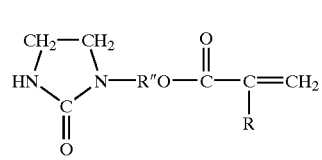

FORMULA I where R=H or $CH_3$;
where $R''=C_1-C_8$ straight or branched alkylene; comprising the sequential steps of:
(1) forming a reaction mixture, comprising:
  (a) hydroxyl alkyl imidazolidin-2-one of Formula III:

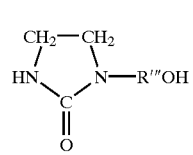

FORMULA III where $R''=C_1-C_8$ straight or branched alkylene;
  (b) 10 to 10,000 ppm, based on weight of said hydroxyl alkyl imidazolidin-2-one of Formula III, of at least one polymerization inhibitor selected from the group consisting of diethylhydroxylamine, p-methoxy phenol, hydroquinone, phenothiazine, 4-hydroxy-2,2,6,6-tetramethyl piperidnyl free radical, 4-methacryloyloxy-2,6,6-tetramethyl piperidinyl free radical, and 4-hydroxy-2,6,6-tetramethyl N-hydroxy piperidine;
(2) adding to said reaction mixture 0.1 to 10 mole % of a transesterification catalyst selected from the group consisting of dibutyl tin oxide, reaction products of dibutyl tin oxide with components in the transesterification of various alcohols with alkyl (meth) acrylates; dibutyl tin dimethoxide, reaction products of dibutyl tin dimethoxide with components in the transesterification of various alcohols with alkyl (meth)acrylates; methanolic magnesium methylate; lithium; lithium carbonate; anhydrous alkali metal hydroxide; hydrates of alkali metal hydroxide; and mixtures thereof;
  wherein said reaction mixture is unagitated when said catalyst is added;
(3) adding to said reaction mixture at least one alkyl (meth)acrylate of Formula II:

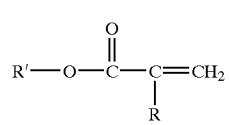

FORMULA II where R=H or $CH_3$; and
where $R'=C_1-C_8$ straight or branched alkyl; under conditions to effect the transesterification of said alkyl (meth)acrylate of Formula II and said hydroxyl alkyl imidazolidin-2-one of Formula III to form a (meth)acrylate of Formula I:

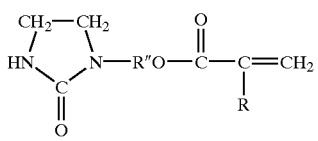

FORMULA I where R=H or CH$_3$;
where R"=C$_1$–C$_8$ straight or branched alkylene; and the alcohol of Formula IV:

R'—OH            FORMULA IV where R'=C$_1$–C$_8$ straight or branched alkyl; and
wherein the mole ratio of said hydroxyl alkyl imidazolidin-2-one of Formula III to total said alkyl (meth)acrylate is from 1:1 to 1:20.

The reaction mixture may further comprise an alkyl (meth)acrylate of Formula II:

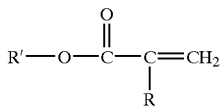

FORMULA II where R=H or CH$_3$; and
where R'=C$_1$–C$_8$ straight or branched alkyl.

The process may further comprise the step of azeotropically removing a mixture of said alkyl (meth)acrylate of Formula II and said alcohol of Formula IV.

The process may further comprise the step of adding water to enable recycling of said transesterification catalyst, if said catalyst has low water solubility.

The process may further comprise the step of recycling the alkyl (meth)acrylate of Formula II.

The process may further comprise the step of distilling the (meth)acrylate of Formula I.

It is not necessary to separate the catalyst or catalyst by-products from the reaction mixture. In addition, it is not necessary to separate the catalyst or catalyst by-products from the reaction mixture, under process conditions where:

(a) excess alkyl (meth)acrylate is used and diluted with water; or
(b) the reaction mixture is treated with water to effect an exchange of the excess alkyl (meth)acrylate with water to produce a mixture of (meth)acrylate of Formula I in water.

There are a number of different ways that the transesterification catalyst may be exposed to increased contact with the hydroxyl alkylene imidazolidin-2-one of Formula III relative to conventional processes. This includes introducing the transesterification catalyst to the hydroxyl alkylene imidazolidin-2-one of Formula III while the reaction mixture is unagitated and wherein the reaction mixture includes:

(a) the hydroxyl alkylene imidazolidin-2-one of Formula III neat (i.e., molten and not provided in solvent, including monomers such as alkyl (meth)acrylate of Formula II); or
(b) the hydroxyl alkylene imidazolidin-2-one of Formula III combined with the alkyl (meth)acrylate of Formula II.

The process of this invention is capable of producing (meth)acrylate monomers of the general formula:

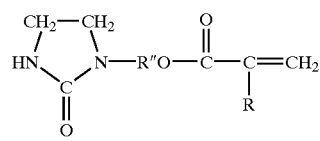

FORMULA I where R H or CH$_3$; and
where R'=C$_1$–C$_8$ straight or branched alkylene. Such (meth)acrylate monomers include N-(2-methacryloyloxyethyl) ethylene urea (MEEU). Such monomers are useful as polymerized units in polymers and provide enhanced properties to such polymers, including adhesion.

One of the reactants that participates in the transesterification reaction is an hydroxyl alkyl imidazolidin-2-one of Formula III:

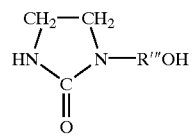

FORMULA III where R'=C$_1$–C$_8$ straight or branched alkylene; Suitable hydroxyl alkylene imidazolidin-2-one of Formula III include hydroxyethyl ethylene urea (HEEU).

The other reactants that participates in the transesterification reaction is an alkyl (meth)acrylate of Formula II:

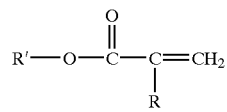

FORMULA II where R=H or CH$_3$; and
where R'=C$_1$–C$_8$ straight or branched alkyl;
Preferred alkyl (meth)acrylates include methyl methacrylate, butyl acrylate and ethyl acrylate. Methyl methacrylate is most preferred.

The mole ratio of hydroxyl alkyl imidazolidin-2-one of Formula III to alkyl (meth)acrylate of Formula II is typically from 1:1 to 1:20, preferably from 1:1 to 1:15, and more preferably from 1:1.2 to 1:10.

The reaction mixture also includes at least one polymerization inhibitor. Suitable polymerization inhibitors include diethylhydroxylamine, p-methoxy phenol, hydroquinone, phenothiazine, 4-hydroxy-2,2,6,6-tetramethyl piperidinyl free radical (4-hydroxy-TEMPO), 4-methacryloyloxy-2,6,6-tetramethyl piperidinyl free radical, and 4-hydroxy-2,6,6-tetramethyl N-hydroxy piperidine and mixtures thereof The amount of inhibitor added to the reaction vessel is typically from 10 to 10,000 parts per million, based on the weight of the hydroxyl alkyl imidazolidin-2-one of Formula III, preferably from 100 to 5,000 ppm, and most preferably 200 to 3,000 ppm.

Suitable transesterification catalysts include dibutyl tin oxide, reaction products of dibutyl tin oxide with components in the transesterification of various alcohols with methyl meth(acrylate) or alkyl (meth)acrylates; dibutyl tin dimethoxide, reaction products of dibutyl tin dimethoxide with components in the transesterification of various alcohols with methyl (meth)acrylate or alkyl (meth)acrylates, methanolic magnesium methylate, lithium, lithium carbonate, anhydrous alkali metal alkoxides (such as lithium hydroxide), hydrates of alkali metal alkoxides (such as lithium hydroxide monohydrate) and mixtures thereof. Anhydrous lithium hydroxide and lithium hydroxide monohydrate are preferred.

The amount of the transesterfication catalyst added to the reaction mixture is typically from 0.1 to 10 mole %, preferably from 0.5 to 7 mole %, and more preferably from 1 to 5 mole %.

The process of the invention utilizes an Oldershaw distillation column. Suitable Oldershaw columns include a 10 plate X 1" (2.54 cm) diameter column, a 5 plate X 1" diameter column, a 10 plate X ½" (1.27 cm) diameter column, and a 32 tray column.

The process of the invention may also utilize a continuous or batch process provided such process permits unagitated contact between the transesterification catalyst and the hydroxyl alkyl imidazolidin-2-one of Formula III. For example, a process may employ an in-line mixer (such as static mixing in a tube reactor) or static impellar. Static mixing in a tube reactor is particularly useful for providing unagitated contact between the transesterification catalyst and molten hydroxyl alkyl imidazolidin-2-one of Formula III.

The transesterification step of the process of the invention may be carried out at a reaction temperature of 60° C. to 140° C., preferably 70° C. to 125° C. and most preferably, 85° C. to 120° C.

The transesterification step of the process of the invention may be carried out at pressures of 760 mm Hg to reduced or elevated pressures, preferably 400 mm Hg to 760 mm Hg.

All ranges used herein are inclusive and combinable.

The following abbreviations are used herein:
HEEU=hydroxyethyl ethylene urea
MMA=methyl methacrylate
Hg=Mercury
DI=deionized
GLC=gas liquid chromatography
° C.=degrees centigrade
$N_2$ =nitrogen
$O_2$=oxygen
(meth)acrylate=methacrylate or acrylate
cc=cubic centimeter
cm=centimeter
hr=hour
mm=millimeter
ml=milliliter
mn=minute
ppm=parts per million
MEEU=N-(2-methacryloyloxyethyl) ethylene urea
MEMEU=N-(2-methacryloyloxyethyl)-N'-(methacryloyl) ethylene urea
HPLC=quantitative high performance liquid chromatography Some embodiments of the present invention will now be described in detail in the following Examples.

EXAMPLES

Example 1 (MEEU/water)

A mixture of 256.8 grams (2.0 mole) of 1-hydroxyethyl ethylene urea (HEEU), 1,124.2 grams (11.2 moles) of methyl methacrylate (MMA) and 0.4 grams (0.00232 moles) of 4-hydroxy-2,2,6,6-tetramethyl piperidinyloxy, free radical (4-hydroxy TEMPO, free radical) was added to a 2-liter 4-necked flask equipped with a temperature indicator, mechanical stirrer, 8% $O_2$-92% $N_2$ sparge inlet and a 1 inch diameter-10 plate Oldershaw column fitted with a distillation head, distillate rate removal-vapor pressure temperature controller, and a graduated distillate receiver. During the dehydration of the batch the mixture was stirred, sparged with 8% $O_2$-92% $N_2$ at a rate of 4 ml/min and heated to reflux under reduced pressure (700 mm Hg) for 30 minutes while removing the MMA-water azeotrope. The temperature at the top of the column was a maximum of 98.7° C. and the temperature in the pot was a maximum of 98° C. At the conclusion of the dehydration of the batch the mixture was cooled to 44° C. and the agitation was stopped. To the two phase mixture was added 0.84 grams (0.02 moles) of lithium hydroxide monohydrate, via a dry glass funnel to avoid liquid and static cling and avoid poor catalyst introduction, followed by 66.3 grams (0.663 moles) of MMA. The mixture was stirred at a moderate agitation rate (60-70 rpm with a blade stirrer) for 20 minutes as the pot temperature was raised to 89° C. The mixture was stirred (240 rpm with a blade stirrer), sparged with 8% $O_2$-92% $N_2$ at a rate of 4 ml/min and refluxed under reduced pressure (700 mm Hg) for 3 hours while removing the MMA-methanol of reaction azeotrope. The progress of the reaction was monitored by refractive index analysis of the MMA-methanol of reaction distillate. During the reaction of the batch, the temperature at the top of the column was 64.8° C. to 98° C. and the temperature in the pot was 89° C. to 98° C.

The conversion of HEEU to N-(2-methacryloyloxyethyl) ethylene urea (MEEU) and by-products was determined to be 84.7% based on the methanol of reaction-MMA azeotrope removal and its analysis for methanol content by refractive index. The conversion of HEEU to MEEU was 81.4%. According to quantitative high-performance liquid chromatography (HPLC) the reaction mixture, a yellow liquid, contained 26.0 weight % MEEU, 66.1 weight % MMA, 1.5 weight % HEEU, and 0.33 weight % N-(2-methacryloyloxyethyl)-N'-(methacryloyl) ethylene urea (MEMEU) and 5.85 % of unintentional by-products.

The MMA was removed from the mixture in vacuo (pot temperature/pressure of 40° C. to 60 ° C./760 to 60 mm Hg) from the stirred and 8% $O_2$-92% $N_2$ sparged mixture. The stirred mixture was cooled to 60° C. to 70° C. and to it was added 396 grams of water. The mixture was stirred at ambient temperature for 15 minutes. According to quantitative high-performance liquid chromatography (HPLC) the mixture, 842.0 grams of product, a yellow liquid, contained 38.3 weight % MEEU, 2.1 weight % MMA, 2.2 weight % HEEU, and 0.48 weight % N-(2-methacryloyloxyethyl)-N'-(methacryloyl) ethylene urea (MEMEU) and 5.26% of unintentional byproducts. By Karl Fischer analysis the product contained 51.3 weight % water.

Example 2 (MEEU/MMA)

A mixture of 261.0 grams (2.0 mole) of 1-hydroxyethyl ethylene urea (HEEU), 1,124.3 grams (11.2 moles) of methyl methacrylate (MMA) and 0.42 grams (0.00232 moles) of 4-hydroxy-2,2,6,6-tetramethyl piperidinyloxy, free radical (4-hydroxy TEMPO, free radical) was added to a 2-liter 4-necked flask equipped with a temperature indicator, mechanical stirrer, 8% $O_2$-92% $N_2$ sparge inlet and a 1 inch diameter-10 plate Oldershaw column fitted with a distillation head, distillate rate removal-vapor pressure temperature controller, and a graduated distillate receiver. During the dehydration of the batch the mixture was stirred, sparged with 8% $O_2$-92% $N_2$ at a rate of 4 ml/min and heated to reflux under reduced pressure (700 mm Hg) for 30 minutes while removing the MMA-water azeotrope. The temperature at the top of the column was a maximum of 98.7° C. and the temperature in the pot was a maximum of 95° C. At the conclusion of the dehydration of the batch the mixture was cooled to 52° C. and the agitation was stopped. To the two phase mixture was added 0.84 grams (0.02 moles) of lithium hydroxide monohydrate, via a dry glass funnel to avoid liquid and static cling and avoid poor catalyst introduction, followed by 74.0 grams (0.74 moles) of MMA. The mixture was stirred at a moderate agitation rate (60–70 rpm with a blade stirrer) for 17 minutes as the pot temperature was raised to 88° C. The mixture was stirred (240 rpm with a blade stirrer), sparged with 8% $O_2$-92% $N_2$ at a rate of 4 ml/min and refluxed under reduced pressure (700 mm Hg) for 2½ hours while removing the MMA-methanol of reaction azeotrope. The progress of the reaction was monitored by refractive index analysis of the MMA-methanol of reaction distillate. During the reaction of the batch the temperature at the top of the column was 64.7° C. to 96.9° C. and the temperature in the pot was 88° C. to 97° C.

The conversion of HEEU to N-(2-methacryloyl oxyethyl) ethylene urea (MEEU) and by-products was determined to be 82.0% based on the methanol of reaction-MMA azeotrope removal and its analysis for methanol content by refractive index. The conversion of HEEU to MEEU was 76.0%. The batch was cooled to ambient temperature and 1,203 g of the product, a yellow liquid, was analyzed by quantitative high-performance liquid chromatography (HPLC). By HPLC analysis the product contained 25.1 weight % MEEU, 67.3 weight % MMA, 2.07 weight % HEEU, and 0.26 weight % N-(2-methacryloyloxyethyl)-N'-(methacryloyl) ethylene urea (MEMEU) and 5.27 weight % of unintentional by-products.

Comparative Example 3 (MEEU/water)

A mixture of 260.1 grams (2.0 mole) of 1-hydroxyethyl ethylene urea (HEEU), 1,124.0 grams (11.2 moles) of methyl methacrylate (MMA) and 0.4 grams (0.00232 moles) of 4-hydroxy-2,2,6,6-tetramethyl piperidinyloxy, free radical (4-hydroxy TEMPO, free radical) was added to a 2 liter 4 necked flask equipped with a temperature indicator, mechanical stirrer, 8% $O_2$-92% $N_2$ sparge inlet and a 1 inch diameter-10 plate Oldershaw column fitted with a distillation head, distillate rate removal-vapor pressure temperature controller, and a graduated distillate receiver. During the dehydration of the batch the mixture was stirred at a rate 240 rpm (blade stirrer), sparged with 8% $O_2$-92% $N_2$ at a rate of 4 ml/min and heated to reflux under reduced pressure (700 mm of Hg) for ~15 minutes while removing the MMA-water azeotrope. The temperature at the top of the column was a maximum of 99.7° C. and the temperature in the pot was a maximum of 95° C. At the conclusion of the dehydration of the batch the mixture was cooled to 43° C. (agitation and 8% $O_2$-92% N2 sparse continued). To the two phase mixture was added 0.43 grams (0.005 moles) of lithium hydroxide monohydrate followed by 69.9 grams (0.699 moles) of MMA. The pot temperature was raised to 89° C. and the mixture was stirred (240 rpm with a blade stirrer), sparged with 8% $O_2$-92% $N_2$ at a rate of 4 ml/min and refluxed under reduced pressure (700 mm of Hg) for ~2½ hours while removing the MMA-methanol of reaction azeotrope. The progress of the reaction was monitored by refractive index analysis of the MMA-methanol of reaction distillate. During the reaction of the batch, the temperature at the top of the column was 64.8° C. to 65.3° C. and the temperature in the pot was 90° C. to 96° C.

The conversion of HEEU to N-(2-methacryloyloxyethyl) ethylene urea (MEEU) and by-products was determined to be 48.2% based on the methanol of reaction-MMA azeotrope removal and its analysis for methanol content by refractive index. The conversion of HEEU to MEEU was about 50%.

The MMA was removed from the mixture in vacuo (pot temperature/pressure of 40 to 60° C./760 to 60 mm of Hg) from the stirred and 8% $O_2$-92% $N_2$ sparged mixture. The stirred mixture was cooled to 60 to 70° C. and to it was added 396.9 grams of water. The mixture was stirred at ambient temperature for 15 minutes. According to quantitative high-performance liquid chromatography (HPLC) the mixture, 842 grams of a product, a yellow liquid, contained 24.6 weight % MEEU, 2.68 weight % MMA, 11.6 weight % HEEU, and 0.07 weight % N-(2-methacryloyloxyethyl)-N'-(methacryloyl) ethylene urea (MEMEU) and 5.92 % of unintentional byproducts. By Karl Fischer analysis the product contained 55.0 weight % water.

As shown in the table below, the process of the invention leads to significantly higher conversions when compared with a conventional process.

| Example Number | Conversion of HEEU to MEEU |
| --- | --- |
| 1 | 81.4% |
| 2 | 76.0% |
| 3 (comparative) | 50% |

What is claimed:
1. A process, comprising the sequential steps of:
 (1) forming a reaction mixture, comprising:
  (a) hydroxyl alkyl imidazolidin-2-one of Formula III:

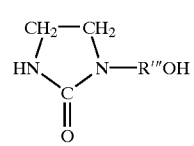

FORMULA III where R"=$C_1$–$C_8$ straight or branched alkylene;
  (b) 10 to 10,000 ppm, based on weight of said hydroxyl alkyl imidazolidin-2-one of Formula III, of at least one polymerization inhibitor selected from the group consisting of diethylhydroxylamine, p-methoxy phenol, hydroquinone, phenothiazine, 4-hydroxy-2,2,6,6-tetramethyl piperidnyl free radical, 4-methacryloyloxy-2,6,6-tetramethyl piperidinyl free radical, and 4-hydroxy-2,6,6-tetramethyl N-hydroxy piperidine;
 (2) adding to said reaction mixture 0.1 to 10 mole % of a transesterification catalyst selected from the group consisting of dibutyl tin oxide, reaction products of dibutyl tin oxide with components in the transesterification of various alcohols with alkyl (meth)acrylates; dibutyl tin dimethoxide, reaction products of dibutyl tin dimethoxide with components in the transesterification of various alcohols with alkyl (meth)acrylates; methanolic magnesium methylate; lithium, lithium carbonate, anhydrous alkali metal hydroxide; hydrates of alkali metal hydroxide; and mixtures thereof;
  wherein said reaction mixture is unagitated when said catalyst is added;
 (3) adding to said reaction mixture at least one alkyl (meth)acrylate of Formula II:

FORMULA II

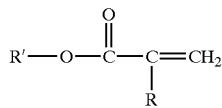

where R=H or CH$_3$; and
where R'=C$_1$–C$_8$ straight or branched alkyl; under conditions to effect the transesterification of said alkyl (meth)acrylate of Formula II and said hydroxyl alkyl imidazolidin-2-one of Formula III to form a (meth)acrylate of Formula I:

FORMULA I

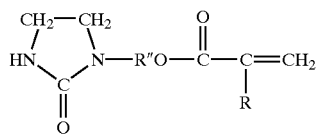

where R=H or CH$_3$;
where R"=C$_1$–C$_8$ straight or branched alkylene; and
and the alcohol of Formula IV:

where R'=C$_1$–C$_8$ straight or branched alkyl; and
wherein the mole ratio of said hydroxyl alkyl imidazolidin-2-one of Formula III to total said alkyl (meth)acrylate is from 1:1 to 1:20.

2. The process of claim 1, wherein said reaction mixture further comprises an alkyl (meth)acrylate of Formula II:

FORMULA II

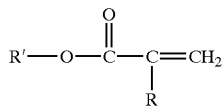

where R=H or CH$_3$; and
where R'=C$_1$–C$_8$ straight or branched alkyl.

3. The process of claim 1 or claim 2, further comprising the step of azeotropically removing a mixture of said alkyl (meth)acrylate of Formula II and said alcohol of Formula IV.

4. The process of claim 1 or claim 2, further comprising the step of adding water to enable recycling of said transesterification catalyst, wherein said transesterification catalyst has low water solubility.

5. The process of claim 1 or claim 2, further comprising the step of recycling the alkyl (meth)acrylate of Formula II.

6. The process of claim 1 or claim 2, further comprising the step of distilling the (meth)acrylate of Formula I.

7. The process of claim 1 or claim 2, wherein said transesterification is carried out at a temperature of 60° C. to 140° C.

8. The process of claim 1 or claim 2, wherein said transesterification is carried out at a pressure of 400 mm Hg to 760 mm Hg.

9. The process of claim 1 or claim 2, wherein said hydroxyl alkyl imidazolidin-2-one of Formula III is hydroxyethyl ethylene urea.

10. The process of claim 1 or claim 2, wherein said transesterification catalyst is anhydrous lithium hydroxide.

11. The process of claim 1 or claim 2, wherein said transesterification catalyst is a monohydrate of lithium hydroxide.

12. The process of claim 1 or claim 2, wherein said transesterification catalyst is introduced via an in-line mixer.

13. The process of claim 1 or claim 2, wherein said transesterification catalyst is introduced via a static impellar.

* * * * *